United States Patent [19]

Klenk et al.

[11] 4,113,773

[45] Sep. 12, 1978

[54] PROCESS FOR THE PRODUCTION OF BENZOYL CYANIDE (I)

[75] Inventors: Herbert Klenk, Hanau; Theodor Lüssling, Constance; Alfred Maierhofer, Allensbach; Heribert Offermanns, Hanau; Hans Wagner, Constance, all of Germany

[73] Assignee: Deutsche Gold- und Silber-Scheideanstalt Vormals Roessler, Frankfurt, Germany

[21] Appl. No.: 802,946

[22] Filed: Jun. 20, 1977

[30] Foreign Application Priority Data

Jun. 3, 1976 [DE] Fed. Rep. of Germany ....... 2624891

[51] Int. Cl.² ............................................. C07C 63/06
[52] U.S. Cl. ................................................ 260/545 R
[58] Field of Search ..................................... 260/545 R

[56] References Cited

U.S. PATENT DOCUMENTS 4,069,252  1/1978  Findeisen et al. ............... 260/545 R

OTHER PUBLICATIONS

Normant et al., Bull. Soc. Chim. France pp. 2402–2403 (1972).

Primary Examiner—Gerald A. Schwartz
Attorney, Agent, or Firm—Cushman, Darby & Cushman

[57] ABSTRACT

Benzoyl cyanide is made by reacting benzoyl chloride with an alkali cyanide in the presence of a carboxylic acid nitrile and a copper (I) salt at a temperature of about 50° to 160° C.

22 Claims, No Drawings

PROCESS FOR THE PRODUCTION OF BENZOYL CYANIDE (I)

BACKGROUND OF THE INVENTION

The invention is directed to a process for the production of benzoyl cyanide by reaction of benzoyl chloride with a metal cyanide at elevated temperature. Benzoyl cyanide is an important intermediate product for the production of herbicides.

It is known to produce benzoyl cyanide by the action of over stoichiometrical amounts of copper (I) cyanide on benzoyl chloride. The reaction is carried out at temperatures up to 80° C. in acetonitrile or benzonitrile or in ether with the addition of over stoichiometrical amounts of lithium chloride or lithium iodide (Normant et al, Bull. Soc. Chim. France (1972) pages 2402–2403) or at temperatures of 220° to 230° C. in the absence of a solvent (Org. Synth. Coll. 3, 112–114). At best these processes give a yield of 65%.

It is also known to convert benzoyl chloride to benzoyl cyanide by means of an alkali cyanide in a two phase system consisting of water and a solvent which is immiscible with water in the presence of a quaternary alkyl ammonium salt (Tetrahedron Letters No. 26 (1974), pages 2275 to 2278). In this process the yield only amounts to 60%.

Furthermore, it is known to produce benzoyl cyanide from benzoyl chloride by reaction with water free hydrogen cyanide and an at least equimolar amount of pyridine (Z. Phys. Chem. 192 (1943), 200–201). This process gives yields of 78%.

A disadvantage of the known process is that there are formed byproducts to a considerable extent, particularly the dimer of benzoyl cyanide (the benzoyloxyphenyl malodinitrile). Consequently, not only is the yield unsatisfactory but also its purity. Benzoyl cyanide can be separated from its dimer only with considerable difficulty and even then only incompletely.

SUMMARY OF THE INVENTION

There has now been found a process for the production of benzoyl cyanide by reaction of benzoyl chloride with metal cyanides at elevated temperature characterized by reaction with an alkali cyanide in the presence of a carboxylic acid nitrile and a copper (I) salt at a temperature of about 50° to 160° C. This process surprisingly gives yields of at least 90%. The benzoyl cyanide is obtained in excellent purity and is particularly as well as free from the dimer.

The reaction according to the invention is carried out at temperatures of about 50° to 160° C., preferably at temperatures of 90° to 150° C., especially at temperatures of 90° to 130° C. Although the pressure can be selected essentially at random (i.e., it is not critical) in order to use a simple apparatus it is advantageous to use a pressure which does not vary substantially from normal pressure, e.g., to use atmospheric pressure. In many cases because of the presence of volatile substances it can be suitable to use an elevated pressure corresponding to the temperature.

In several cases it can be advantageous to add an inert solvent as a diluent. As such inert solvents there can be used for example hydrocarbons, e.g., aromatic hydrocarbons such as benzene, toluene or xylene as well as mesitylene, ethyl benzene, cumene, p-cymene, t-butyl benzene or 1,3,5-triethyl benzene or aliphatic hydrocarbons such as ligroin with a boiling range of about 90° to 140° C., octane or decane or cyclic hydrocarbons such as decalin, cyclohexane and tetralin or halogenated hydrocarbons, particularly chlorinated aromatic or aliphatic hydrocarbons such as chlorobenzene, symmetrical tetrachloroethane, carbon tetrachloride, trichloroethylene, trimethylene bromide, ethylene dibromide. Also as the solvent there can be used for example ether, e.g., dioxane, dibutyl ether, dioxolane, ethylene glycol diethyl ether, ethylene glycol dibutyl ether, ethylene glycol dimethyl ether or esters, e.g., alkyl esters such as butyl acetate, propyl acetate, amyl acetate, isobutyl acetate, octyl acetate, ethyl propionate, methyl butyrate. ethyl butyrate or methyl valerate. When an inert solvent is employed, the amount is not critical but it can be used for example in an amount of 10 to 5000 ml per mol of benzoyl chloride.

According to the invention the reaction takes place with alkali cyanides. Preferably there is used sodium cyanide or potassium cyanide. There also can be used lithium cyanide. Generally it is suitable to employ at least a stoichiometric amount of cyanide. Advantageously there is used about 1.05 to 3.0 equivalents of cyanide, especially 1.05 to 1.5 equivalents of cyanide, per mole of benzoyl chloride.

The reaction takes place in the presence of carboxylic acid nitriles. There can be used nitriles which are liquid under the reaction conditions and which are not changed. Especially suited are saturated aliphatic monocarboxylic acid nitriles of saturated aliphatic monocarboxylic acids with 2 to 6 carbon atoms, e.g., alkyl nitriles, especially acetonitrile and isobutyronitrile. Other suitable nitriles include propionitrile, butyronitrile, valeronitrile,, capronitrile, caprylonitrile or lauronitrile or unsubstituted aryl nitriles such as benzonitrile, o-toluonitrile, p-toluonitrile or m-toluonitrile.

The reaction furthermore takes place in the presence of copper (I) salts. There can be used both simple and complex copper (I) salts, particularly for example copper (I) cyanide, copper (I) chloride, copper (I) bromide and potassium tetracyanocuprate (I). There can also be used copper (I) fluoride, copper (I) iodide, copper (I) sulfate, copper (I) thiocyanate and sodium tetracyanocuprate (I).

The amount of nitrile and copper (I) salt to use depends in a given case on the type of nitrile and copper (I) salt and the reaction conditions, such as temperature and pressure, and in a given case on the type and amount of the solvent used as a diluent.

Generally it is suitable to add at least 0.05 mole of nitrile per mole of benzoyl chloride. Although the nitrile can be used in a many times molar excess, it is advantageous to use not more than about 2 moles of nitrile per mole of benzoyl chloride. Preferably there are used per mole of benzoyl chloride about 0.1 to 1.0 mole of nitrile, especially 0.1 to 0.5 mole of nitrile.

It is generally suitable to use about 0.5 to 1.0 equivalent of copper (I) salt per mole of benzoyl chloride. Preferably there is employed 0.05 to 0.5 equivalent of copper (I) salt per mole of benzoyl chloride.

The cyanide is added as alkali cyanide. If the copper (I) salt used is a cyanide there can be eliminated entirely or partially an equivalent amount of alkali cyanide. However, it is generally advantageous to include not more than about 0.5 equivalent of cyanide in the form of copper salts.

Unless otherwise indicated all parts and percentages are by weight.

DESCRIPTION OF THE PREFERRED EMBODIMENTS

The materials employed can comprise, consist essentially of or consist of those set forth.

EXAMPLE 1

There were mixed in a reaction vessel provided with a reflux condenser 140.5 grams (1.0 mole) of benzoyl chloride, 54 grams (1.1 mole) of sodium cyanide, 9 grams (0.1 mole) of copper (I) cyanide, 25 ml of xylene and 7.5 ml (0.14 mole) of acetonitrile. The mixture was heated to 130° C. with stirring. The mixture was held for 3 hours at this temperature and then cooled to 15° C. The salts separated thereby, chiefly sodium chloride, were filtered off and washed with 25 ml of xylene. The filtrate was fractionally distilled under reduced pressure. There were recovered 119.5 grams of pure benzoyl cyanide, corresponding to a yield of 91% based on the benzoyl chloride employed. The benzoyl cyanide had a boiling point of 113° to 117° C. at 43 mbar.

EXAMPLE 2

The procedure was the same as in Example 1 but there were employed in addition to 140.5 grams (1.0 mole) of benzoyl chloride, 59 grams (1.2 moles) of sodium cyanide, 30 grams (0.3 mole) of copper (I) chloride, 25 ml of xylene and 15 ml (0.3 mole) of acetonitrile. There were recovered 118 grams of benzoyl cyanide, corresponding to a yield of 90% based on the benzoyl chloride employed. The benzoyl cyanide had a boiling point of 114° to 117° C. at 43 mbar.

EXAMPLE 3

The procedure was the same as in Example 1 except that in place of xylene and acetonitrile there were used 25 ml of ligroin (boiling range 110° to 140° C.) and 25 ml (0.3 mole) of isobutyronitrile. The reaction took place at 130° C. There were recovered 120 grams of benzoyl cyanide, corresponding to a yield of 92% based on the benzoyl chloride employed. The benzoyl cyanide had a boiling point of 113° to 115° C. at 40 mbar.

EXAMPLE 4

The procedure was the same as in Example 1 except there were used 26.2 ml (0.5 mole) of acetonitrile. The reaction took place at 105° C. There were recovered 119 grams of benzoyl cyanide, corresponding to a yield of 91% based on the benzoyl chloride employed. The benzoyl cyanide had a boiling point of 115° to 117° C. at 45 mbar.

What is claimed is:

1. In a process for preparing benzoyl cyanide by reacting an alkali metal cyanide with benzoyl chloride in the presence of a copper (I) salt the improvement comprising carrying out the reaction at a temperature of about 50° to 160° C. in the presence of a carboxylic acid nitrile inert under the reaction conditions.

2. A process according to claim 1 wherein the copper (I) salt is copper (I) cyanide copper (I) chloride, copper (I) bromide or potassium tetracyanocuprate (I).

3. A process according to claim 2 wherein the alkali cyanide is sodium cyanide or potassium cyanide.

4. A process according to claim 2 wherein there is used 0.1 to 3.0 equivalents of cyanide per mole of benzoyl chloride.

5. A process according to claim 4 wherein there is used 1.05 to 1.5 equivalents of cyanide per mole of benzoyl chloride.

6. A process according to claim 5 wherein there is used 0.1 to 0.5 mole of carboxylic acid nitrile per mole of benzoyl chloride.

7. A process according to claim 6 wherein there is used 0.05 to 0.5 equivalents of copper (I) salt per mole of benzoyl chloride.

8. A process according to claim 2 wherein there is used 0.05 to 2 moles of carboxylic acid nitrile per mole of benzoyl chloride.

9. A process according to claim 8 wherein the nitrile is a liquid alkyl nitrile.

10. A process according to claim 9 wherein the nitrile has 2 to 6 carbon atoms.

11. A process according to claim 10 wherein the nitrile is acetonitrile or isobutyronitrile.

12. A process according to claim 8 wherein there is used 0.01 to 0.5 mole of carboxylic acid nitrile.

13. A process according to claim 2 wherein there is used 0.05 to 1.0 equivalent of copper (I) salt per mole of benzoyl chloride.

14. A process according to claim 13 wherein there is used 0.05 to 0.5 equivalent of copper (I) salt per mole of benzoyl chloride.

15. A process according to claim 2 wherein the temperature is 90° to 130° C.

16. A process according to claim 2 carried out in the presence of an inert organic solvent as a diluent.

17. A process according to claim 16 wherein the inert solvent is a hydrocarbon or halohydrocarbon.

18. A process according to claim 2 wherein the inert solvent is an aromatic hydrocarbon, an aliphatic hydrocarbon, a chlorinated aromatic hydrocarbon or a chlorinated aliphatic hydrocarbon.

19. A process according to claim 18 wherein the inert solvent is benzene, toluene, xylene, ligroin boiling at about 90° to 140° C., chlorobenzene, dichlorobenzene or tetrachloroethane.

20. A process according to claim 2 wherein the copper (I) salt is copper (I) chloride, copper (I) bromide or potassium tetracyanocuprate (I).

21. A process according to claim 2 wherein the copper (I) salt is copper (I) cyanide.

22. A process according to claim 1 wherein the copper (I) salt is copper (I) cyanide, copper (I) chloride, copper (I) bromide, potassium tetracyanocuprate (I), copper (I) fluoride, copper (I) iodide, copper (I) sulfate, copper (I) thiocyanate or sodium tetracyanocuprate (I).

* * * * *

UNITED STATES PATENT OFFICE
CERTIFICATE OF CORRECTION

Patent No. 4,113,773     Dated September 12, 1978

Inventor(s) Herbert KLENK, Theodor LUSSLING, Alfred MAIERHOFER

It is certified that error appears in the above-identified patent and that said Letters Patent are hereby corrected as shown below:

Column 2, line 57, change 0.5 to 0.05 column 4, line 28, change 0.01 to 0.1

Signed and Sealed this

Sixth Day of February 1979

[SEAL]

Attest:

RUTH C. MASON
Attesting Officer

DONALD W. BANNER
Commissioner of Patents and Trademarks